(12) United States Patent
Crist et al.

(10) Patent No.: US 7,817,277 B2
(45) Date of Patent: Oct. 19, 2010

(54) FIBER OPTIC PROBE AND RELATED APPARATUS, SYSTEMS AND METHODS FOR MAKING OPTICS-BASED MEASUREMENTS OF LIQUID SAMPLES

(75) Inventors: George Bryan Crist, Wilmington, NC (US); C. J. Anthony Fernando, Chapel Hill, NC (US)

(73) Assignee: Varian, Inc., Santa Clara, CA (US)

( * ) Notice: Subject to any disclaimer, the term of this patent is extended or adjusted under 35 U.S.C. 154(b) by 99 days.

(21) Appl. No.: 12/009,759

(22) Filed: Jan. 22, 2008

(65) Prior Publication Data

US 2009/0185187 A1    Jul. 23, 2009

(51) Int. Cl.
*G01N 21/00* (2006.01)
(52) U.S. Cl. .................. 356/436; 356/414; 356/440; 250/227.11
(58) Field of Classification Search ................ 356/436, 356/414, 440, 319; 385/12; 422/82.05, 82.09, 422/65; 250/227.11
See application file for complete search history.

(56) References Cited

U.S. PATENT DOCUMENTS

| 4,240,751 | A | * | 12/1980 | Linnecke et al. ............. 356/409 |
| 4,934,811 | A | * | 6/1990 | Watts et al. .................... 356/73 |
| 5,684,296 | A | * | 11/1997 | Hamblin et al. ......... 250/227.11 |
| 6,174,497 | B1 | * | 1/2001 | Roinestad et al. ......... 422/82.05 |
| 6,580,506 | B2 | | 6/2003 | Inman, Jr. |
| 6,661,512 | B2 | * | 12/2003 | Fernando et al. ............. 356/319 |
| 7,332,128 | B2 | * | 2/2008 | Fernando et al. ............. 422/100 |
| 2003/0086823 | A1 | * | 5/2003 | Fernando et al. .............. 422/81 |
| 2003/0197125 | A1 | * | 10/2003 | De Saro et al. ......... 250/339.07 |

* cited by examiner

*Primary Examiner*—Tarifur R. Chowdhury
*Assistant Examiner*—Isiaka O Akanbi
(74) *Attorney, Agent, or Firm*—Bella Fishman

(57) ABSTRACT

A fiber-optic probe includes first and second optical fibers disposed in a body, a liquid sampling region between ends of the fibers and a reflector, and apertures communicating with the sampling region. The probe may be inserted in media in a vessel. Optical signals are transmitted through the first fiber, the sampling region and second fiber. The sampling region is offset from other parts of the probe so that bubbles or particulates flow out from the sampling region without being obstructed by the probe.

13 Claims, 6 Drawing Sheets

FIBER OPTIC PROBE AND RELATED APPARATUS, SYSTEMS AND METHODS FOR MAKING OPTICS-BASED MEASUREMENTS OF LIQUID SAMPLES

FIELD OF THE INVENTION

The present invention relates generally to making an optics-based measurement of a liquid sample by utilizing fiber optics to route optical signals to and from the liquid sample. Such optical signals may be utilized to measure a property of the liquid sample such as, for example, the concentration of an analyte of interest. More particularly, the present invention relates to a fiber-optic probe useful for making such measurements.

BACKGROUND OF THE INVENTION

Optical transport techniques may be utilized to direct a beam or pulse of light from a light source (e.g., lamp, light-emitting diode or LED, laser, laser diode or LD, etc.) to a test site to irradiate sample material and, subsequently, conduct a resulting optical beam or pulse generated at the test site to a suitable light receiving device (e.g., an optical detector or sensor such as a photocell). Irradiation of the sample results in analytical information being encoded in the optical signal that is transmitted to the detector. This analytical information may be chemical or biological in nature. For example, the analytical information can be utilized to identify a particular analyte, i.e., a component of interest, that is resident within a sample material contained at the test site and to determine the concentration of the analyte. Examples of analytical signals include, among others, emission, absorption, scattering, refraction, and diffraction of electromagnetic radiation over differing ranges of spectra or wavelengths. Measurement and encoding of analytical signals may occur in sample cells, cuvettes, tanks, pipes, flow cells, or solid sample holders of various designs.

Many of these analytical signals are measured through spectroscopic techniques. Spectroscopy generally involves irradiating a sample with electromagnetic radiation (e.g., light), measuring an ensuing consequence of the irradiation (e.g., absorption, emission, or scattering), and interpreting the measured parameters to provide the desired information. An example of an instrumental method of spectroscopy entails the operation of a spectrophotometer to scan the sample. The spectrophotometer typically includes both the light source and the optical detector as well as other optical signal-processing hardware. The spectrophotometer may scan the sample while the sample resides in a sample cell within the spectrophotometer. Alternatively, the spectrophotometer may route optical signals to a remotely situated probe as described further below. Depending on the type of sample material and spectral analysis desired, the light source may be configured to produce ultraviolet (UV) radiation, visible light or both (UV-vis), or in other cases infrared (IR) or near infrared (NIR) radiation. The light source in combination with the irradiated sample serves as the analytical signal generator. In response to irradiation, the analytical signal is generated in the form of an optical signal that is attenuated as a consequence of analytes of the sample absorbing some of the electromagnetic energy. The attenuated signal is received by the light receiving detector and the detector converts the optical signal into an electrical signal. The electrical signal is then processed as needed, such as to correlate the level of attenuation with the concentration of the analytes within the sample by implementing known hardware and software means. Data resulting from these processes may then be sent to a readout or display device.

For spectrophotometers operating according to UV-visible molecular absorption methods, the quantity measured from a sample is the magnitude of the radiant power or flux supplied from a radiation source that is absorbed by the analyte species of the sample. Ideally, a value for the absorbance A can be validly calculated as being directly proportional to analyte concentration through Beer's law:

$$A = -\log T = -\log \frac{P}{P_0} = abc,$$

where T is the transmittance, $P_0$ is the magnitude of the radiant power incident on the sample, P is the magnitude of the diminished (or attenuated) radiant power transmitted from the sample, a is the absorptivity, b is the pathlength of absorption, and c is the concentration of the absorbing species.

Thus, utilizing the foregoing method, the concentration of the analyte may be determined from the absorbance value, which in turn may be calculated from the ratio of measured radiation transmitted and measured radiation incident. Moreover, a true absorbance value may be obtained by measuring a reference or blank media sample and taking the ratio of the radiant power transmitted through the analyte sample to that transmitted through the blank sample.

One technique for preparing a sample for optical scanning is to implement spectroscopy in conjunction with dissolution testing. Dissolution testing is often performed as part of preparing and evaluating soluble materials, particularly pharmaceutical dosage forms (e.g., tablets, capsules, and the like) consisting of a therapeutically effective amount of active drug carried by an excipient material. Typically, dosage forms are dropped into test vessels that contain dissolution media of a predetermined volume and chemical composition. For instance, the composition may have a pH factor that emulates a gastro-intestinal environment. Dissolution testing can be useful, for example, in studying the drug release characteristics of the dosage form or in evaluating the quality control of the process used in forming the dose. To ensure validation of the data generated from dissolution-related procedures, dissolution testing is often carried out according to guidelines approved or specified by certain entities such as United States Pharmacopoeia (USP), in which case the testing must be conducted within various parametric ranges. The parameters may include dissolution media temperature, the amount of allowable evaporation-related loss, and the use, position and speed of agitation devices, dosage-retention devices, and other instruments operating in the test vessel.

As a dosage form is dissolving in the test vessel of a dissolution system, optics-based measurements of samples of the solution may be taken at predetermined time intervals through the operation of analytical equipment such as a spectrophotometer as noted above. The analytical equipment may determine analyte (e.g. active drug) concentration and/or other properties. The dissolution profile for the dosage form under evaluation—i.e., the percentage of analytes dissolved in the test media at a certain point in time or over a certain period of time—can be calculated from the measurement of analyte concentration in the sample taken. In one specific method employing a spectrophotometer, sometimes referred to as the sipper method, dissolution media samples are pumped from the test vessel(s) to a sample cell contained within the spectrophotometer, scanned while residing in the sample cell, and in some procedures then returned to the test vessel(s). In another more recently developed method, sometimes referred to as the in situ method, a fiber-optic "dip probe" is inserted directly in a test vessel. The dip probe includes one or more optical fibers that communicate with the spectrophotometer. In the in situ technique, the spectrophotometer thus does not require a sample cell as the dip probe serves a similar function. Measurements are taken directly in the test vessel and thus optical signals rather than liquid samples are transported between the test vessel and the spectrophotometer. Optical fibers, or light pipes, facilitate the transport of the optical signals.

The spectrophotometer typically includes some sort of optical information selector to sort out or discriminate the desired optical signal from the several potentially interfering signals produced by the encoding process. For instance, a wavelength selector can be used to discriminate on the basis of wavelength, or optical frequency. In addition, data processing devices operating in conjunction with the spectrophotometer may implement software algorithms to improve the accuracy and quality of the data being produced. Nonetheless, non-analytical components of the media being irradiated, such as bubbles and particulates, are still a significant source of analytical errors and noise in conventional systems, as described below.

FIG. 1 is a schematic view representative of a typical fiber-optics based liquid sample measurement system 100. A dip probe 104 is inserted into a test vessel 108 and communicates with a spectrophotometer 112 via a light-transmitting fiber-optic cable 116 and a light-returning fiber-optic cable 120. At its lower or distal end, the dip probe 104 has a sample target region 124 defined between a glass, fused silica or quartz lens 128 and a mirror 132 spaced from the lens 128 by an axial gap. The lens 128 also serves as a seal to prevent liquid from entering the main body portion of the dip probe 104. The ends of the light-transmitting fiber-optic cable 116 and the light-returning fiber-optic cable 120 are coupled with the lens 128 in a manner suitable for enabling the transmission of optical signals between the fiber-optic ends and the lens 128. The other end of the light-transmitting fiber-optic cable 116 is coupled to a light source 136 of the spectrophotometer 112. The other end of the light-returning fiber-optic cable 120 is coupled to a detection means of the spectrophotometer 112 such as a photodiode amplifier/detector 140. The spectrophotometer 112 usually includes an interference filter 144 or similar component interposed between the light-returning fiber-optic cable 120 and the detector 140. The dip probe 104 has one or more side openings 148 between the lens 128 and the mirror 132.

In use, the dip probe 104 is inserted into the test vessel 108 far enough that the sample target region 124 is completely submerged in liquid media 152 contained in the test vessel 108. In this manner, the sample target region 124 is positioned in open communication with the liquid media 152 via the side opening(s) 148, thereby allowing absorbance measurements to be taken directly in the test vessel 108. A beam of light emitted by the light source 136 is guided by the light-transmitting fiber-optic cable 116 along the direction of arrow A into the sample target region 124. This beam of light passes through the media residing in the sample target region 124, is reflected by the mirror 132, and is thereby redirected into the light-returning fiber-optic cable 120 along the direction indicated by arrow B. The light beam then passes through the interference filter 144 and returns to the spectrophotometer 112 where the signal is processed by the detector 140.

During operation, non-analytical components 164 such as bubbles and particulates are produced in the liquid media 152 from a number of sources. Dosage forms such as tablets include not only the therapeutically active component for which absorbance data are sought (i.e., analytes) but also excipients or fillers. Thus, the dissolution of dosage forms disperses particulates of such non-analytical components 164 throughout the liquid media 152 along with the analytes. Bubbles or vapor pockets may be generated by the operation of an agitation device in the test vessel 108 such as a paddle or magnetic bar-type stirrer, by the insertion of the probe 104 into the test vessel 108, by the operation of the agitation device in the presence of the probe 104 due to these structures residing in the test vessel 108, by poorly controlled heating of the liquid media 152, etc. Unfortunately, probes 104 designed as illustrated in FIG. 1 are not capable of removing such non-analytical components 164 from the sample target region 124. The non-analytical components 164 tend to interfere with the UV scan and consequently produce inaccurate data. For instance, non-analytical components 164 may accumulate at the underside of the lens 128. Appropriate software programs can be used to compensate for the inconsistencies caused by the particulates. However, because each sample dosage form has unique particulate features, every sample being tested requires a separate algorithm for correcting the errors caused by the particulates of the dosage form.

An example of an in-situ fiber-optic dip probe similar to that illustrated in FIG. 1 is disclosed in U.S. Pat. No. 6,174,497. The probe disclosed in U.S. Pat. No. 6,174,497 is intended to reduce analytical errors and noise sources attending the use of such probe. For instance, the disclosure recommends that the probe be kept submerged in the test vessel over the course of the entire dissolution run to reduce the occurrence of air bubbles resulting from insertion and avoid fouling due to drying while the probe is removed. Nonetheless, the fact that the probe is constantly submerged means that hydrodynamic influences can still affect the release rate of the dosage formulation being tested. In addition, the probe in one embodiment is integrated within the shaft of an agitation device to reduce the effects related to flow aberration, as in such a case only the stirring shaft/dip probe combination resides in the test vessel. This arrangement, nevertheless, still requires the use of software algorithms to correct for noise-related physical events. Moreover, regardless of whether the probe is integrated with a stirring shaft or provided separately, no provision is made for eliminating interference by bubbles and particulates within the sample target region of the probe and thus analytical errors are still a problem.

Another recent example of an in-situ fiber-optic method associated with dissolution testing is disclosed in U.S. Pat. No. 6,580,506, which utilizes a U-shaped dip probe that is inserted into a test vessel. One leg of the U-shaped probe contains a source optical fiber and the other leg contains the return optical fiber. A gap between the ends of the fibers is defined at the base of the U-shape, across which the light beam is transmitted through the media of the test vessel. This patent emphasizes the need to avoid the use of mirrors, but introduces other problems. Because two optical fibers are provided in two separate structures (i.e., legs) and one fiber must transmit its optical signal across the gap and be received by the other fiber, the two legs must be aligned with each other with a significant degree of precision. The optical alignment achieved by this design is less than optimal. Even the slightest movement of the opposing pair of fiber ends may cause a significant loss of light transmission. The resulting adverse effect on performance may worsen over time and may vary from one instance of operation to another. Moreover, the alignment of the two legs requires that the legs be interconnected by structural cross-members. The resulting design introduces a number of geometric/structural features in the test vessel that may increase the amount of turbulence or flow aberration in the dissolution media and thus increase analytical errors.

Accordingly, there continues to be a need for improved fiber-optic probes and related apparatus and methods that produce accurate analytical signals from liquid samples.

SUMMARY OF THE INVENTION

To address the foregoing problems, in whole or in part, and/or other problems that may have been observed by persons skilled in the art, the present disclosure provides methods, processes, systems, apparatus, instruments, and/or devices, as described by way of example in implementations set forth below.

According to one implementation, a fiber-optic probe for making optics-based measurements on liquid samples is provided. The probe includes a body. The body includes a first body portion and a second body portion oriented at an angle relative to the first body portion. The second body portion has a plurality of apertures. At least one of the apertures is disposed about a first axis along which bubbles rise. The second body portion includes an optical signal-transmitting boundary and an optical signal-reflecting boundary spaced from the optical signal-transmitting boundary along a second axis generally orthogonal to the first axis. The optical signal-transmitting boundary and the optical signal-reflecting boundary define a liquid sampling region therebetween in fluid communication with the plurality of apertures. The apertures are positioned to establish a flow path for liquid and bubbles through the liquid sampling region generally along the first axis. The flow path is offset from the first body portion by a distance along the second axis. A first optical fiber is disposed in the body and terminates at a first fiber end in optical communication with the optical signal-transmitting boundary. A second optical fiber is disposed in the body and terminates at a second fiber end in optical communication with the optical signal-reflecting boundary. The probe establishes an optical path running through the first optical fiber, through the optical signal-transmitting boundary along the second axis, through the liquid sampling region while intersecting the flow path, to the optical signal-reflecting boundary, reflecting from the optical signal-reflecting boundary back through the liquid sampling region, back through the optical signal-transmitting boundary along the second axis, and through the second optical fiber.

According to another implementation, an apparatus for making optics-based measurements on liquid samples is provided. The apparatus includes a light source, a detector, and a fiber-optic probe. The probe includes a body. The body includes a first body portion and a second body portion oriented at an angle relative to the first body portion. The second body portion has a plurality of apertures. At least one of the apertures is disposed about a first axis along which bubbles rise. The second body portion includes an optical signal-transmitting boundary and an optical signal-reflecting boundary spaced from the optical signal-transmitting boundary along a second axis generally orthogonal to the first axis. The optical signal-transmitting boundary and the optical signal-reflecting boundary define a liquid sampling region therebetween in fluid communication with the plurality of apertures. The apertures are positioned to establish a flow path for liquid and bubbles through the liquid sampling region generally along the first axis. The flow path is offset from the first body portion by a distance along the second axis. A first optical fiber is disposed in the body and terminates at a first fiber end in optical communication with the optical signal-transmitting boundary. A second optical fiber is disposed in the body and terminates at a second fiber end in optical communication with the optical signal-reflecting boundary. The system establishes an optical path running from the light source and through the first optical fiber, through the optical signal-transmitting boundary along the second axis, through the liquid sampling region while intersecting the flow path, to the optical signal-reflecting boundary, reflecting from the optical signal-reflecting boundary back through the liquid sampling region, back through the optical signal-transmitting boundary along the second axis, and through the second optical fiber to the detector.

According to another implementation, a method for making optics-based measurements on liquid samples is provided. A liquid sampling region of a probe is submerged in a liquid contained in a vessel. The liquid sampling region is purged of bubbles by permitting bubbles to rise through the liquid out from the liquid sampling region along a first direction. An optical signal of a first intensity is transmitted through a first optical fiber in a probe body of the probe along a first optical transmitting path, and to the liquid sampling region of the probe along a second optical transmitting path generally orthogonal to the first direction. The optical signal is transmitted through the liquid sampling region predominantly along a second direction generally orthogonal to the first direction, reflected off of an optical signal-reflecting boundary of the probe, and transmitted back through the liquid sampling region predominantly along the second direction to produce an optical signal of a second intensity. The second intensity is attenuated relative to the first intensity in proportion to a concentration of sample analytes in the liquid. The optical signal of the second intensity is transmitted from the liquid sampling region to a second optical fiber in the probe body, through the second optical fiber along a first optical receiving path generally orthogonal to the first direction, and along a second optical receiving path angled relative to the first optical receiving path.

Other devices, apparatus, systems, methods, features and advantages of the invention will be or will become apparent to one with skill in the art upon examination of the following figures and detailed description. It is intended that all such additional systems, methods, features and advantages be included within this description, be within the scope of the invention, and be protected by the accompanying claims.

BRIEF DESCRIPTION OF THE DRAWINGS

The invention can be better understood by referring to the following figures. The components in the figures are not necessarily to scale, emphasis instead being placed upon illustrating the principles of the invention. In the figures, like reference numerals designate corresponding parts throughout the different views.

DETAILED DESCRIPTION OF THE INVENTION

In general, terms such as "communicate" and "in . . . communication with" (for example, a first component "communicates with" or "is in communication with" a second component) are used herein to indicate a structural, functional, mechanical, electrical, signal, optical, magnetic, electromagnetic, ionic or fluidic relationship between two or more components or elements. As such, the fact that one component is said to communicate with a second component is not intended to exclude the possibility that additional components may be present between, and/or operatively associated or engaged with, the first and second components.

The subject matter disclosed herein generally relates to the analysis of liquid media by optical means. Examples of implementations of methods and related devices, apparatus, and/or systems are described in more detail below with reference to FIGS. 2-6. Some of these examples are described in the context of dissolution testing. However, any process that involves the use of optical signals in acquiring data from sample media may fall within the scope of this disclosure.

Figure 2:
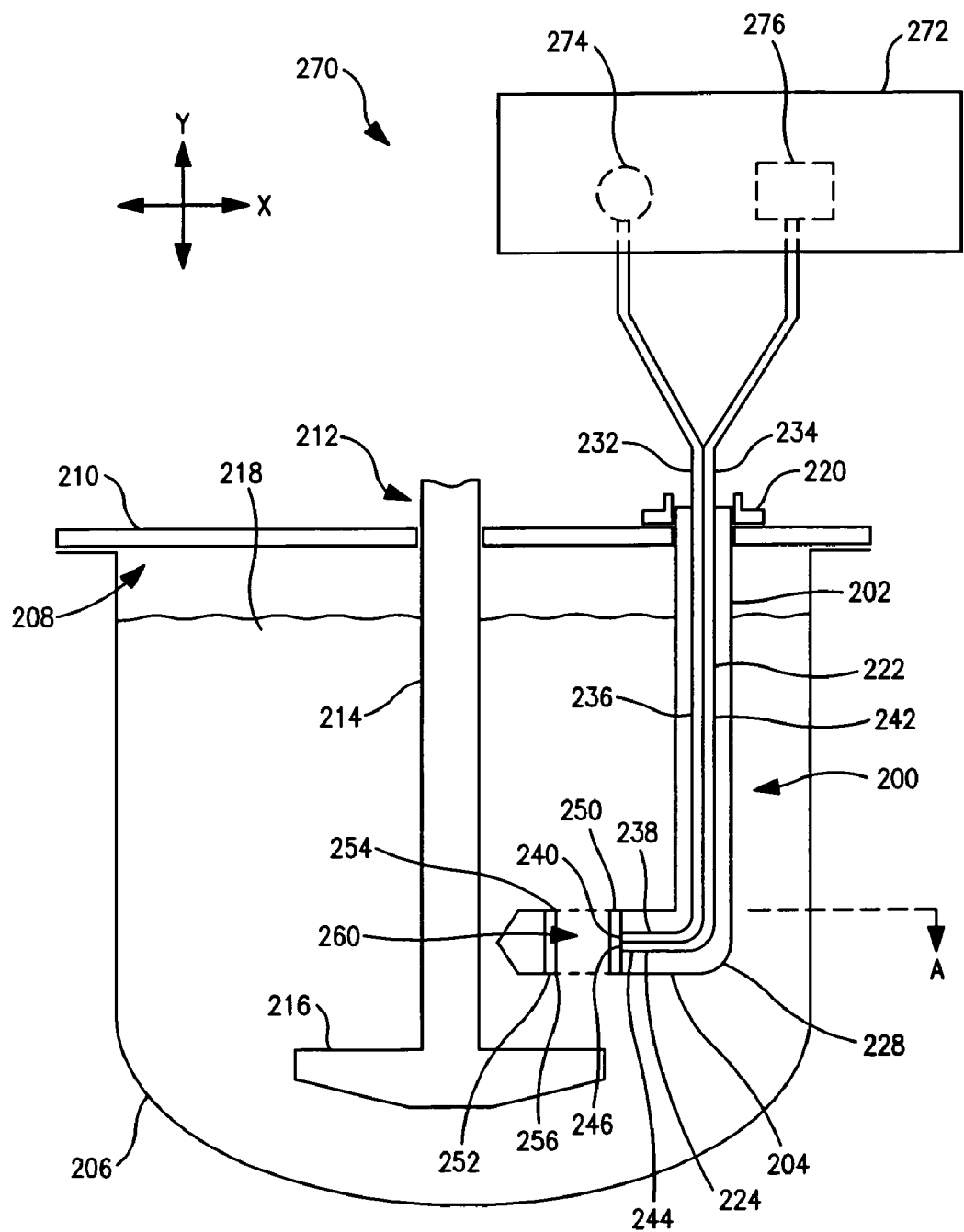
FIG. 2 is a schematic/cross-sectional view of an example of a fiber-optic probe and an example of a related apparatus or system according to an implementation of the present disclosure.

FIG. 2 includes a cross-sectional elevation view of an example of fiber-optic probe 200 for making optics-based measurements on liquid samples according to an implementation of the present disclosure. For illustrative purposes, FIG. 2 also depicts a first or X axis and a second or Y axis as an arbitrarily located coordinate frame of reference. The probe 200 includes a main body or structure that includes a first body portion 202 and a second body portion 204.

In use, the probe 200 may be inserted into a vessel 206 such as test vessel typically utilized in analytical procedures such as dissolution testing. The vessel 206 may include an upper opening 208, which in some implementations may be covered by a vessel cover 210 suitably affixed across the vessel opening 208 to reduce the loss of media due to evaporation. One or more other instruments or devices 212 may be inserted in the vessel 206 as needed for a particular use. Examples of other instruments or devices 212 include, but are not limited to, USP-type apparatus (stirring paddles, baskets, nets, cylinders, etc.), liquid (media, solvent, reagent, etc.) supply or return conduits, liquid aspiration or sampling conduits, agitation/stirring/mixing devices, dosage delivery devices, dosage form holders, other types of measurement or sensing probes (e.g., temperature, pH concentration, video camera, etc.), and the like. In the example of FIG. 2, an instrument or device 212 in addition to the probe 200 is represented by a stirring device that includes a shaft or spindle 214 and a paddle 216 that operates in the vessel 206 along with the probe 200.

In use, the probe 200 may be inserted far enough into the vessel 206 such that the second body portion 204 is submerged in liquid media 218 contained in the vessel 206. The position of the probe 200 relative other nearby structures such as the vessel 206 and another instrument 212 may be fixed in any suitable manner. For example, the vessel cover 210 (if provided) may include a fitting 220 that engages the probe 200. Alternatively, the probe 200 may be fixed by a structure external to the vessel 206 and extend through an opening of the vessel cover 210 (if provided), in which case the fitting 220 may function as a seal to prevent evaporation loss if desired. Alternatively, the probe 200 may be alternately inserted into and removed from the vessel 206 by manual means or any suitable automated or semi-automated means. For example, movement of the probe 200 may be effected by an automated or semi-automated component of a dissolution test apparatus or other analytical apparatus.

In some implementations, the first body portion 202 of the probe 200 may be elongated (or have a predominant length) generally or substantially along the X-axis. The second body portion 204 may be elongated (or have a predominant length) generally or substantially along the Y-axis. In this context, terms such as "generally" and "substantially" encompass the respective longitudinal axes of the first and second body portions 202 and 204 being oriented exactly along the X-axis or Y-axis, as well as the first and/or second body portions 202 and 204 deviating by some minor degree from the corresponding X-axis or Y-axis, due for example to manufacturing tolerances or variations in the positioning of the probe 200 relative to nearby structures. In one example, the first body portion 202 may deviate from the X-axis by up to +/−10 degrees and the second body portion 204 may deviate from the Y-axis by up to +/−10 degrees. The first body portion 202 has a first bore 222 that may be oriented generally along the X-axis. The second body portion 204 has a second bore 224 that may be oriented generally along the Y-axis. Accordingly, the second bore 224 may be oriented generally orthogonal to the first bore 222. Again, terms such as "generally" and "substantially" in this context encompass implementations in which the first bore 222 and the second bore 224 are exactly mutually orthogonal as well as deviations of up to +/−10 degrees from the 90-degree orientation. More generally, the second body portion 204 may be oriented at an angle relative to the first body portion 202, and the second bore 224 may be oriented at an angle relative to the first bore 222. The first bore 222 openly transitions to the second bore 224. The transition from the first body portion 202/first bore 222 to the second body portion 204/second bore 224 may be sharply defined or may be gradual with some radius of curvature. In some implementations, the probe 200 may be considered as including an intermediate or transition portion 228 interconnecting the first body portion 202/first bore 222 and the second body portion 204/second bore 224, such as in the nature of a 90-degree elbow.

The probe 200 also includes a first optical fiber 232 (or optical transmitting fiber) and a second optical fiber 234 (or optical receiving fiber). The first optical fiber 232 includes a an optical transmitting portion or length 236 that extends through the first bore 222 and another optical transmitting portion or length 238 that extends through the second bore 224. The optical transmitting portion 238 terminates at a first optical fiber end 240. The second optical fiber 234 includes an optical receiving portion or length 242 that extends through the first bore 222 and another optical receiving portion or length 244 that extends through the second bore 224. The optical receiving portion 244 terminates at a second optical fiber end 246. All or part of the optical transmitting portion 238 and the optical receiving portion 244, or at least the first optical fiber end 240 and the second optical fiber end 246, is disposed about the second axis and may be generally orthogonal to the first axis.

The probe 200 further includes an optical-transmitting boundary (or surface, or window) 250 located in the second body portion 204. The optical-transmitting boundary 250 may be provided by a suitable optical-transmitting element such as, for example, a material composed of glass, fused silica, quartz, or the like. The optical-transmitting boundary 250 may be a lens such as, for example, a plano-convex lens, and may be optimized for a certain type of light transmission (e.g., UV-optimized). The first optical fiber end 240 and the second optical fiber end 246 are optically coupled to the optical-transmitting boundary 250 by any means suitable for ensuring transmission of optical signals between the optical-transmitting boundary 250 and the first and second optical fiber ends 240 and 246 with a level of efficiency acceptable for communication of optical information. As an example, the first optical fiber end 240 and the second optical fiber end 246 may be directly bonded or attached to the optical-transmitting boundary 250. As an example, the interfaces between the optical-transmitting boundary 250 and the first and second optical fiber ends 240 and 246 may be butt joints or similar alternatives. As another example, a lens or lenses may be interposed between the optical-transmitting boundary 250 and the first and second optical fiber ends 240 and 246. The probe 200 further includes an optical-reflecting boundary (or surface or mirror) 252 located in the second body portion 204 and spaced at a distance from the optical-transmitting boundary 250 along the second axis. One or more apertures 254 and 256 are formed in the second body portion 204 in the gap between the optical-transmitting boundary 250 and the optical-reflecting boundary 252. By this configuration, a liquid sampling region 260 is defined in the second body portion 204 of the probe 200 that in use is in open fluid communication with the interior of the vessel 206 via the apertures 254 and 256. Upon submerging the second body portion 204 of the probe 200 in the liquid media 218 contained in the vessel 206, the liquid media 218 fills the liquid sampling region 260.

While the cross-sectional elevation view of FIG. 2 illustrates an aperture 254 located at an upper surface of the second body portion 204 and an opposing aperture 256 located at a lower surface of the second body portion 204, it will be understood that additional apertures may be located at side surfaces of the second body portion 204. The number and respective positions of the apertures are such as to facilitate the free flow of liquid media 218 through the liquid sampling region 260 and particularly to promote the escape of particulates and bubbles from the liquid sampling region 260 as described further below. In some implementations, the above-noted first axis is the vertical axis or the direction along which bubbles rise through the liquid sampling region 260.

FIG. 2 also includes a cross-sectional elevation view of an example of an apparatus or system 270 for making optics-based measurements on liquid samples according to an implementation of the present disclosure. The apparatus 270 may include the probe 200, or the probe 200 and the vessel 206, as well as analytical instrumentation 272 with which the probe 200 optically communicates. In the specific example, a source or transmitter 274 of electromagnetic energy (e.g., a light source) communicates with the first optical fiber 232 and a receiver 276 of electromagnetic energy (e.g., an optical detector or sensor) communicates with the second optical fiber 234. Examples of the light source 274 include, but are limited to, one or more lamps (e.g., deuterium, xenon, etc.), LEDs, lasers or laser diodes (LDs), etc. Examples of the optical detector or sensor 276 include, but are limited to, one or more photocells, photodiodes, etc. The optical detector 276, or both the light source 274 and the optical detector 276, may be integrated in an analytical instrument 272 such as, for example, a spectrophotometer. The apparatus 270 may include more than one probe 200 (operating in a corresponding number of vessels 206), more than one light source 274, and more than one optical detector 276. Depending on the number of probes 200 relative to light sources 274 and optical detectors 276, the apparatus 270 may include appropriate means for routing optical signals to and from the probes 200 (e.g., optical switches, multiplexers, demultiplexers, etc.). In some implementations, one or more vessels 206 are supported in a dissolution test apparatus.

In use, the light source 274 transmits one or more optical signals of an initial intensity through the first optical fiber 232. The optical signal or signals propagate from the first fiber end 240, through the optical-transmitting boundary 250 and to the liquid sampling region 260 of the probe 200. The optical signals may be transmitted on a continuous or pulsed basis. Optical signals are reflected by the optical-reflective boundary 252 of the probe 200 and propagate back toward the optical-transmitting boundary 250. In passing though the liquid sampling region 260, the optical signals are attenuated (i.e., reduced) in correlation with the absorbance of electromagnetic energy by analyte components of the media 218 residing in the liquid sampling region 260 at the time of irradiation by the optical signals. Consequently, the attenuated optical signals are received at the second fiber end 246 of the second optical fiber 234 and transmitted through the second optical fiber 234 to the optical detector 276. As appreciated by persons skilled in the art, the attenuated optical signals received by the optical detector 276 may be converted to electrical signals and processed as necessary to produce useful data indicative of the concentration of analytes in the liquid media 218 at a given time and the dissolution rate of a dosage form being tested in the vessel 206 over time. Additionally or alternatively, the optical data may be utilized to derive other useful data respecting the analytes and media 218 contained in the vessel 206.

Figure 1:
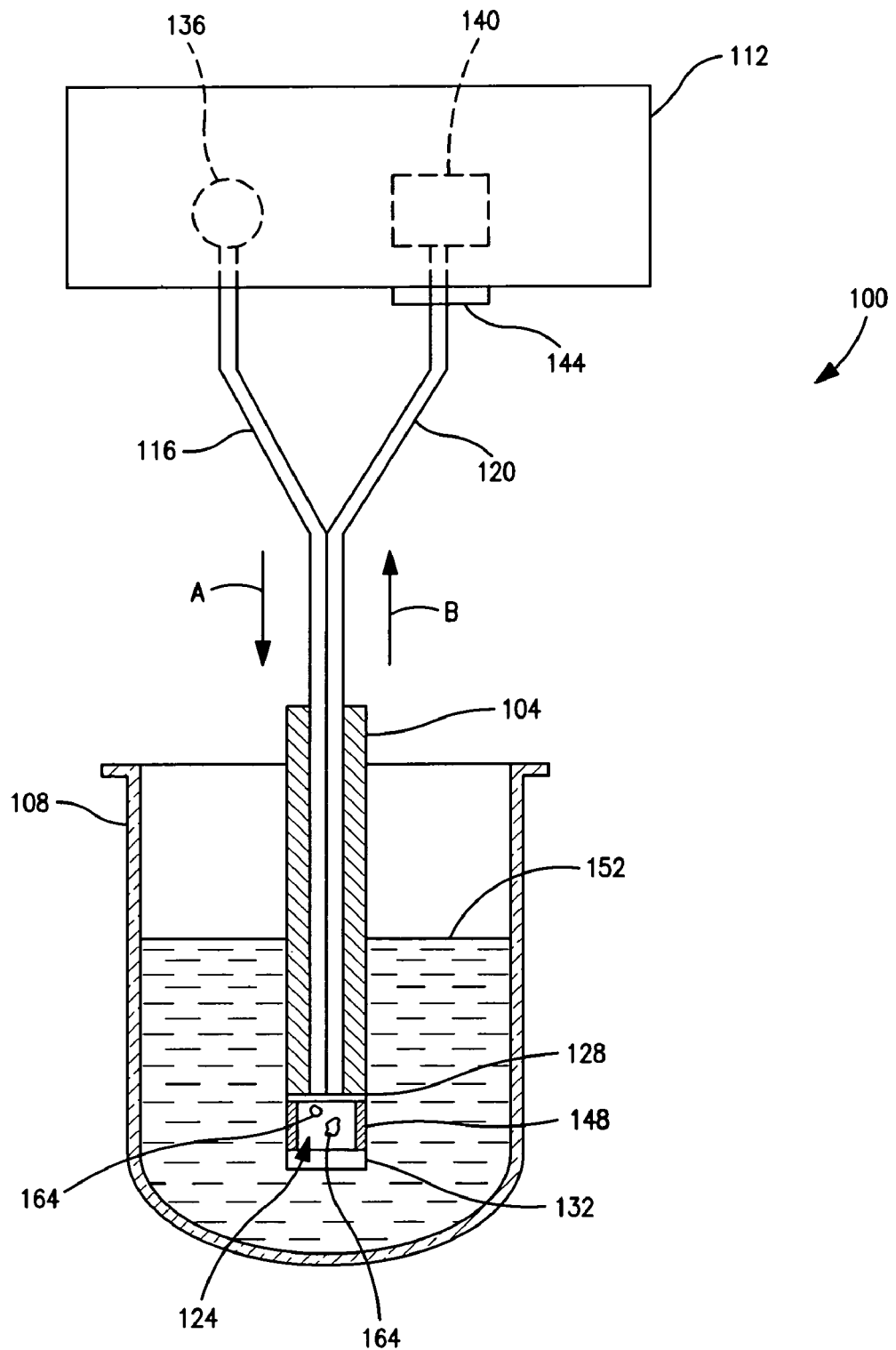
FIG. 1 is a schematic/cross-sectional view of a fiber-optic probe of known, conventional design.

In comparing the straight-configured probe 104 illustrated in FIG. 1 to the 90-degree configured probe 200 illustrated in FIG. 2, it can be seen that the probe 200 taught herein retains geometric simplicity and takes up minimal volume within the vessel 206. Accordingly, detrimental flow aberrations and adverse hydrodynamic effects due to the existence of the probe 200 in the vessel 206 are minimized such that the quality of optics-based data may be maintained and even enhanced due to the ability to purge particulates and bubbles from the liquid sampling region 260 as described below. Such advantages may be facilitated by the use of the vertically-oriented optical-reflective boundary 252, contrary to the U-shaped probe described earlier in the present disclosure. It will be noted that the probe 200 is enlarged in FIG. 2 for illustrative purposes. The probe 200 in practice may be much smaller relative to the vessel 206 and other instruments 212 in the vessel 206.

Figure 3:
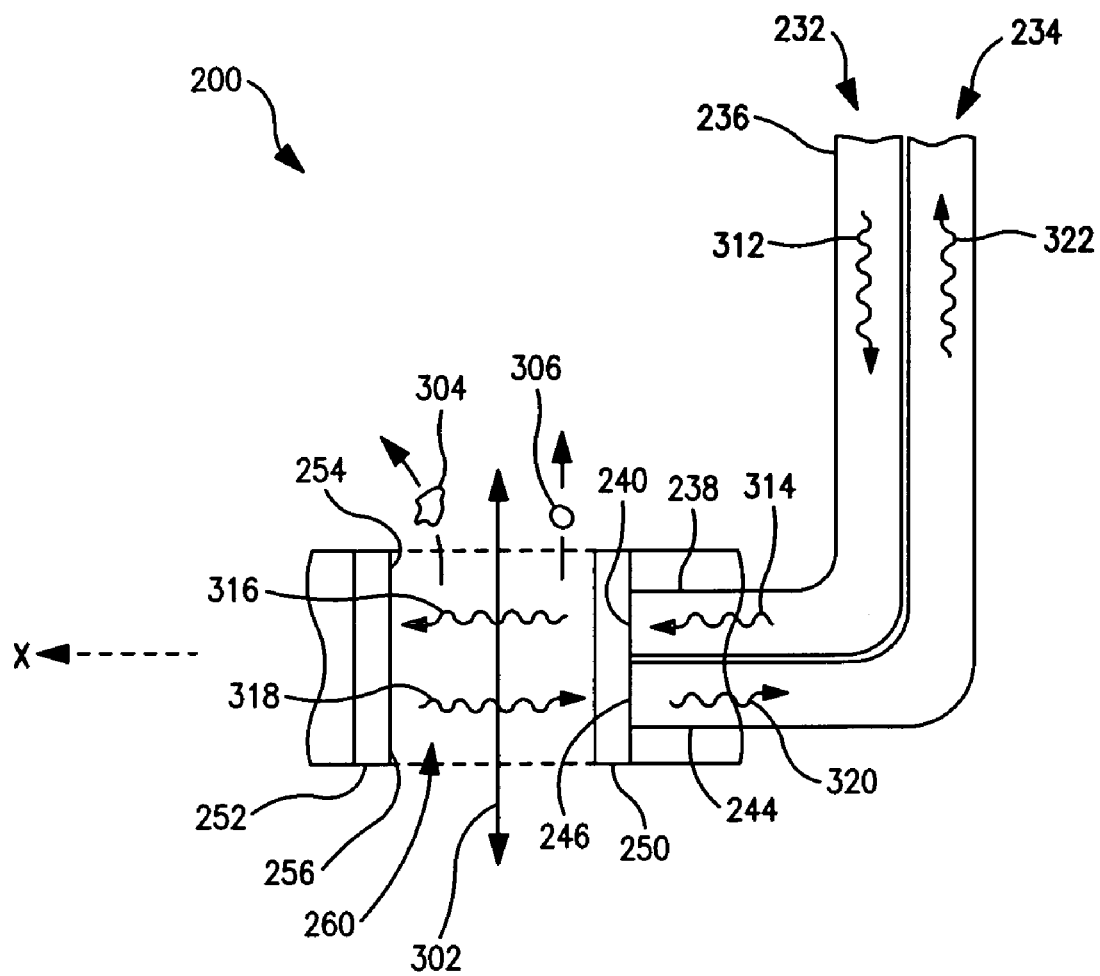
FIG. 3 is a cross-sectional elevation view of a portion of the probe illustrated in FIG. 2 that includes a liquid sampling region.

FIG. 3 is a partially schematic, partially cross-sectional view of the portion of the probe 200 in the vicinity of the liquid sampling region 260. An arrow 302 directed along the first axis represents the flow of liquid media through the liquid sampling region 260 via the apertures 254 and 256 specifically illustrated, with the understanding that flow may also occur in other directions (e.g., including directions into and out from the drawing sheet of FIG. 3) in implementations where one or more side apertures are provided. The angled configuration of the probe 200 promotes the purging of particulates 304 and bubbles 306 from the liquid sampling region 260. In particular, due to buoyancy effects bubbles 306 are able to rise straight up from the liquid sampling region 260 via the upper aperture 254. The offset or off-axis position of the liquid sampling region 260 relative to other parts of the probe 200 ensures that no part of the probe 200 obstructs the path of particulates 304 and bubbles 306 out from the liquid sampling region 260. Consequently, particulates 304 and bubbles 306 do not accumulate on the optical-transmitting boundary 250 or any other surfaces associated with the liquid sampling region 260. Moreover, the tendency for particulates 304 and bubbles 306 to interfere with the transmission of optical signals through the liquid sampling region 260 and concomitantly impair optics-based measurements is significantly lowered.

Continuing with FIG. 3, the probe 200 in this example is configured as described herein to establish an optical path that intersects the flow of analyte-laden media in the liquid sampling region 260 in directions generally along the second axis and oriented generally orthogonal to the vertical direction. In the illustrated example, the optical path may be described as follows. An optical source signal, provided for example by the light source 274 illustrated in FIG. 2, travels downwardly through one transmitting portion 236 of the first optical fiber 232 along a first axis that may correspond or generally correspond to the vertical direction, as depicted by an arrow 312. The optical source signal then travels through the other transmitting portion 238 of the first optical fiber 232 along a second axis generally orthogonal to the vertical direction, as depicted by an arrow 314. The optical source signal then exits from the first optical fiber end 240 and travels through the optical-transmitting boundary 250 into the liquid sampling region 260. Through the liquid sampling region 260, the optical signal continues to travel in a resultant direction generally along the second axis toward the optical-reflecting boundary 252, as depicted by an arrow 316. The optical signal is then reflected by the optical-reflecting boundary 252 and travels back through the liquid sampling region 260 in a resultant direction generally along the second axis toward the optical-transmitting boundary 250, as depicted by an arrow 318. The attenuated optical return signal enters the second optical fiber end 246 via the optical-transmitting boundary 250 and continues to travel generally along the second axis through one receiving portion 244 of the second optical fiber 234, as depicted by an arrow 320. The optical return signal then travels upwardly through the other receiving portion 242 of the second optical fiber 234 along the first axis, as depicted by an arrow 322. The optical return signal may then be routed from the probe 200 to a suitable optical detector 276 such as illustrated in FIG. 2 and processed further.

Figure 4:
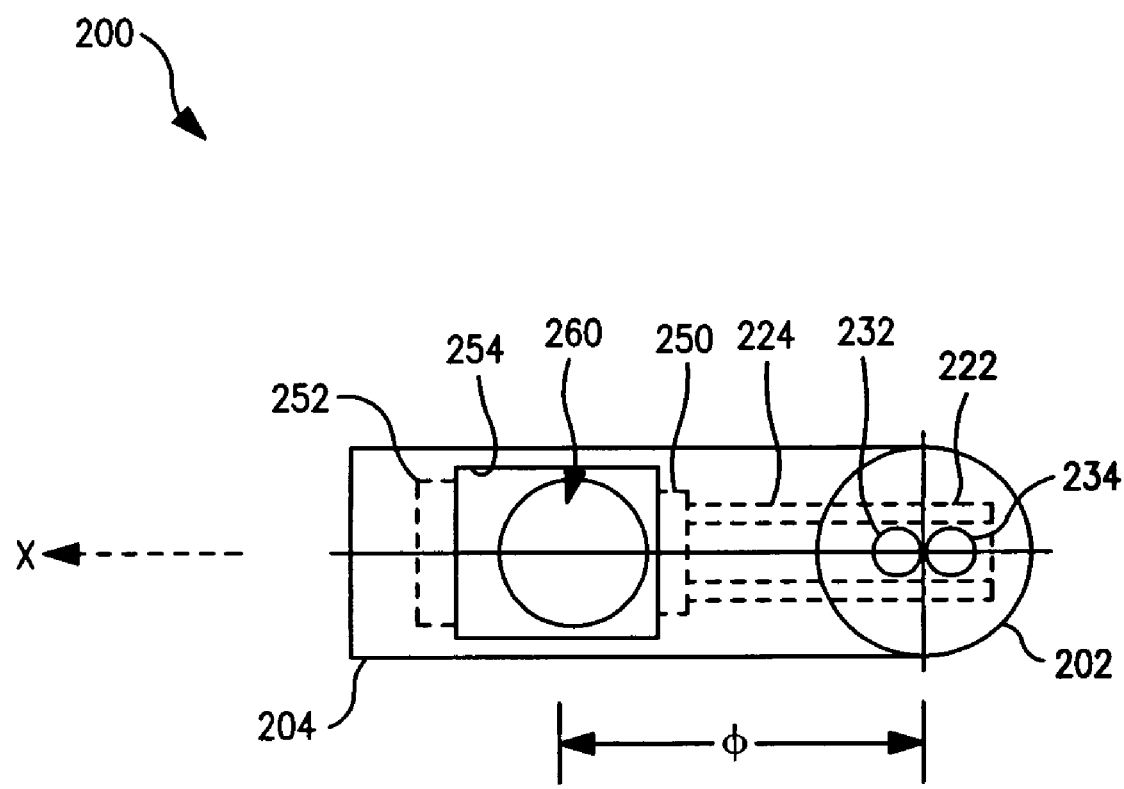
FIG. 4 is a cross-sectional top view of the probe illustrated in FIG. 2, taken along line A.

FIG. 4 is a top cross-sectional view of the probe 200 taken along line A in FIG. 2. In the illustrated example, the first and second body portions 202 and 204 of the probe 200 are cylindrical but in other implementations may be rectilinear or have other shapes. In the illustrated example, the first and second optical fibers 232 and 234 are positioned immediately adjacent to each other throughout the first and second body portions 202 and 204, are positioned on either side of the central longitudinal axis of the first body portion 202 in alignment with the central longitudinal axis of the second body portion 204, and are positioned one on top of the other on either side of the central longitudinal axis of the second body portion 204 (see FIGS. 2 and 3). It will be understood, however, that the first and second optical fibers 232 and 234 may be positioned differently in other implementations. The first and second optical fibers 232 and 234 and their respective ends should be positioned within the probe 200 so as to efficiently route optical signals to and from the liquid sampling region 260. Moreover, no specific limitations are placed on the shapes and sizes of the first and second bores 222 and 224 respectively formed through the first and second body portions 202 and 204 so long as the first and second bores 222 and 224 adequately accommodate the provision and function of the first and second optical fibers 232 and 234. Furthermore, the apertures 254 associated with the liquid sampling region 260 may be sized and shaped in any manner suitable for establishing the flow of particulates and bubbles out from the liquid sampling region 260 as described above. Finally, FIG. 4 illustrates the offset or off-axis positioning of the liquid sampling region 260 and its associated apertures 254 relative to the first body portion 202. As a demonstrative example, FIG. 4 illustrates an offset distance d along the X axis between the center of the upper aperture 254 and the central longitudinal axis of the first body portion 202.

Figure 5:
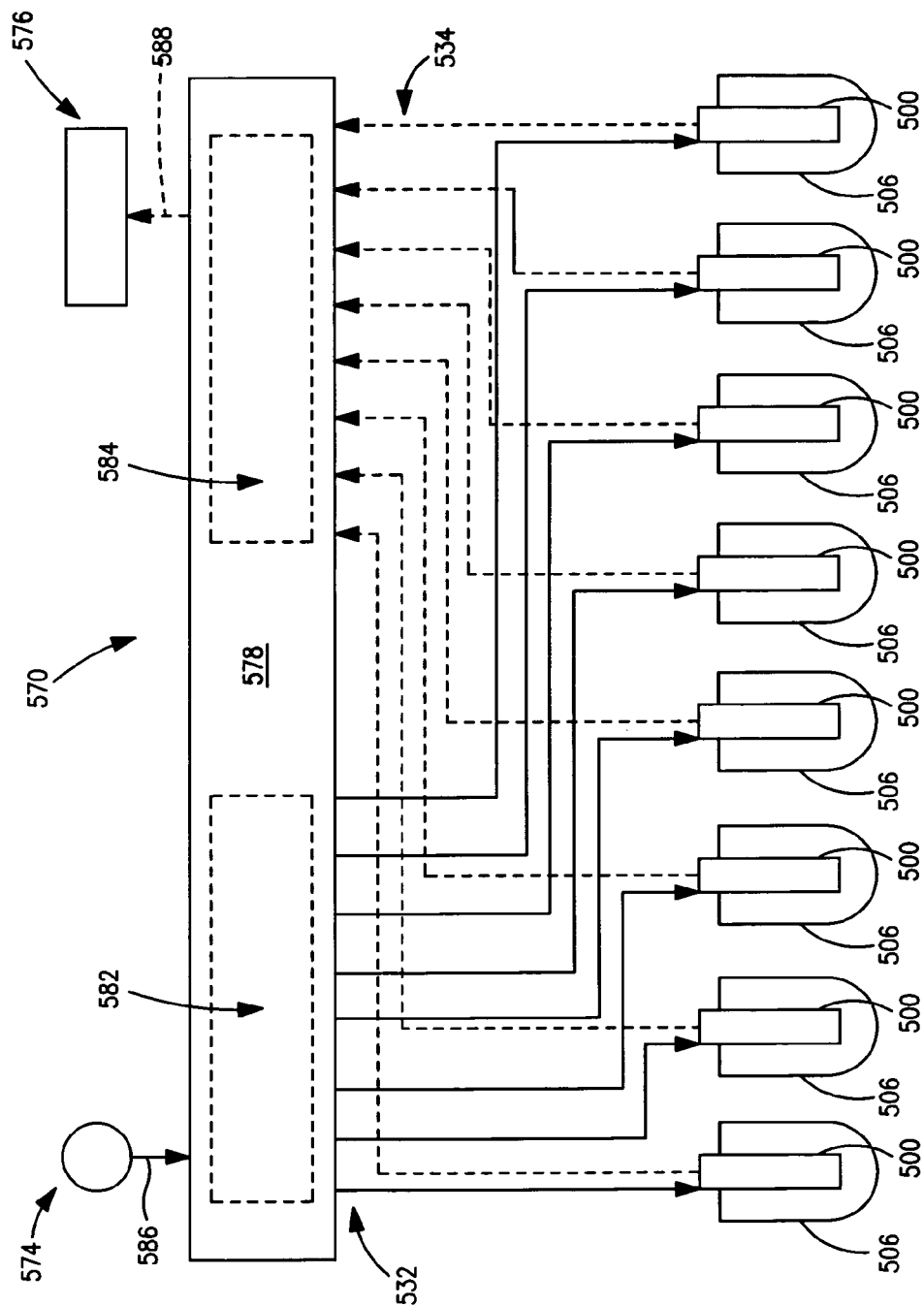
FIG. 5 is a schematic view of an example of an apparatus or system including a plurality of probes according to an implementation of the present disclosure.

FIG. 5 schematically illustrates an example of an apparatus or system 570 for making optics-based measurements on liquid samples according to another implementation of the present disclosure. The apparatus 570 may include a plurality of fiber-optic probes 500 insertable in a corresponding plurality of vessels 506. Each probe 500 may include a first optical fiber 532 and a second optical fiber 534. Each probe 500 may be structured and function similarly to the probe 200 described above and illustrated in FIGS. 2-4. The apparatus 570 enables optics-based testing of a plurality of samples simultaneously. One of the vessels 506 may contain blank media and another vessel 506 may contain standard media as appreciated by persons skilled in the art. One or more light sources 574 and one or more detectors 576 may be employed. If the number of light sources 574 and/or detectors 576 is less than the number of probes 500 and vessels 506 being operated, a suitable optical channel selection device 578 may be provided that may include a suitable demultiplexer 582 and/or multiplexer 584 respectively communicating with the light source(s) 574 and optical detector(s) 576 via one or more optical input lines 586 and one or more optical output lines 588.

Figure 6:
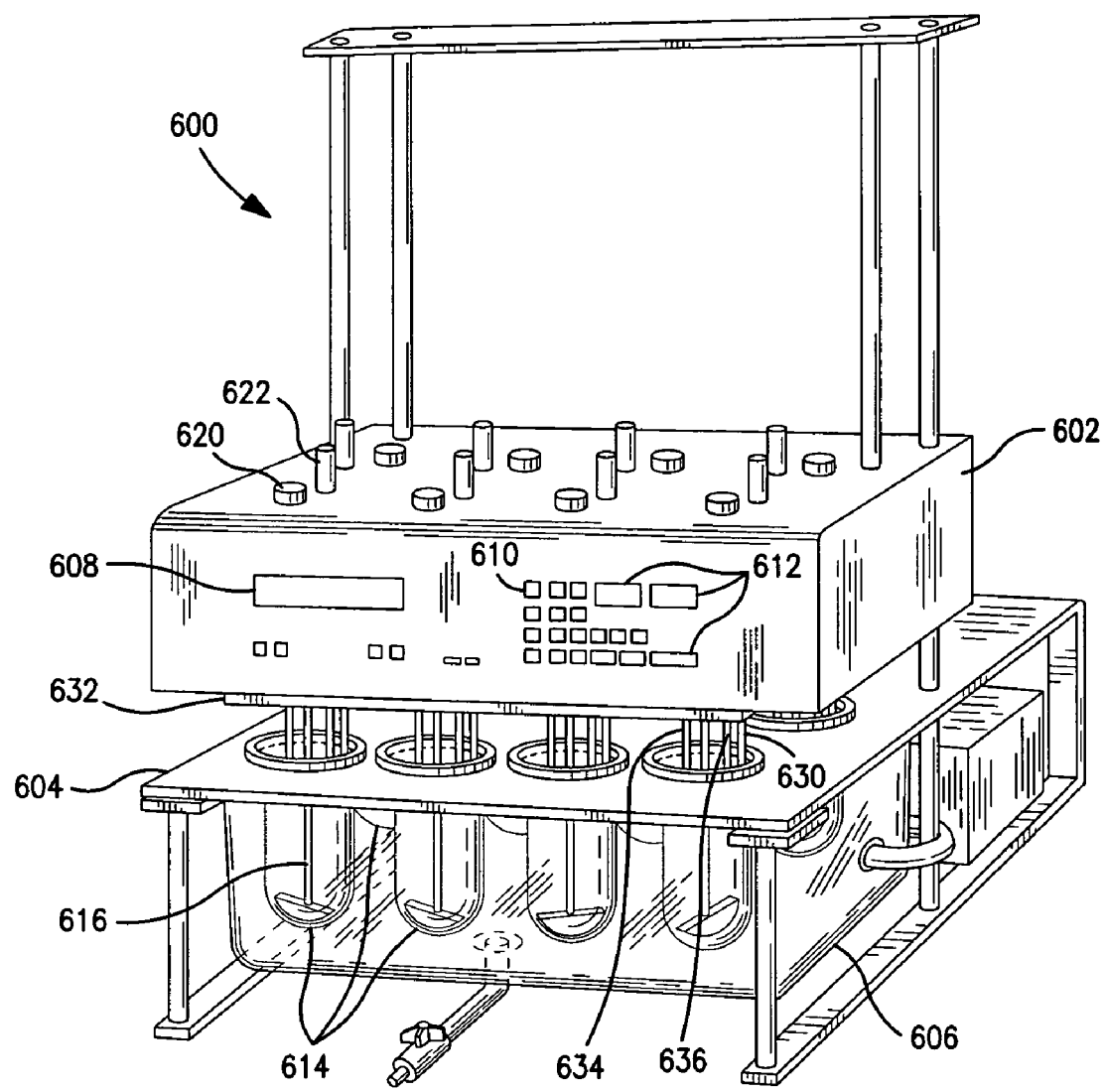
FIG. 6 is a perspective view of an example of a dissolution test apparatus including a plurality of probes according to an implementation of the present disclosure.

FIG. 6 is a perspective view of an example of a dissolution test apparatus 600 that may form a part of or operate in combination with an apparatus or system for making optics-based measurements on liquid samples according to another implementation of the present disclosure. The dissolution test apparatus 600 may include a main housing or head assembly 602 that may include a programmable systems control module. The head assembly 602 may be situated above a vessel plate 604 and a water bath container 606, and is typically motor-driven for vertical movement toward and away from the vessel plate 604. Peripheral elements located on the head assembly 602 may include an LCD display 608 for providing menus, status and other information; a keypad 610 for providing user-inputted operation and control of spindle speed, temperature, test start time, test duration and the like; and readouts 612 for displaying information such as RPM, temperature, elapsed run time, or the like. The vessel plate 604 supports a plurality of vessels 614 extending into the interior of water bath container 606. One of the vessels 614 may be utilized as a blank vessel and another as a standard vessel as noted above. Water is heated and circulated through water bath container 606 ordinarily by means such as external heater and pump modules. Alternatively, the dissolution test apparatus 600 may be a waterless heating design in which each vessel 614 is directly heated by some form of heating element disposed in thermal contact with the wall of the vessel 614.

The vessels 614 are typically locked and centered in place on vessel plate 604 by means such as ring lock devices or clamps (not shown). Vessel covers (not shown) may be provided as noted previously. A stirring element 616 including a motor-driven spindle and paddle may operate in each vessel 614. Individual clutches 620 may be provided to alternately engage and disengage power to each stirring element 616 by manual, programmed or automated means. A dosage delivery module 622 may be utilized to preload and drop dosage units (e.g., tablets) into each vessel 614 at prescribed times and media temperatures. Fiber-optic probes 630 such as described above may also be provided in one or more of the vessels 614.

An automated or semi-automated assembly 632 may be provided for lowering and raising the stirring elements 616, probes 630, and other instruments 632 and 636 such as, for example, cannulas of various types and functions, temperature probes such as thermistors, pH probes, etc. into and out of each respective vessel 614. Additionally or alternatively, the automated assembly 632 may itself be vertically movable between the head assembly 602 and the vessel plate 604.

In a typical operation, each vessel 614 is filled with a predetermined volume of dissolution media. Dosage units are dropped either manually or automatically into each media-containing vessel 614, and each stirring element 616 (or other agitation or USP-type device) is rotated within its vessel 614 at a predetermined rate and duration within the test solution as the dosage units dissolve. In other types of tests, a cylindrical basket (not shown) loaded with a dosage unit is substituted for each stirring element 616 and rotates within the test solution. For any given vessel 614, the temperature of the test solution must be maintained at a prescribed temperature (e.g., approximately 37+/−0.5 degrees C.) if certain USP dissolution methods are being conducted. The mixing speed of the stirring element 616 must also be maintained. Solution temperature is maintained by immersion of each vessel 614 in the water bath of water bath container 606, or alternatively by direct heating as described previously. The probes 630 may operate continuously in the vessels 614 during test runs. Alternatively, the probes 630 may be lowered manually or by the automated assembly 632 into the corresponding vessels 614, left to remain in the vessels 614 only while sample measurements are being taken at allotted times, and at all other times kept outside of the media contained in the vessels 614. In some implementations, submerging the probes 630 in the vessel media at intervals may reduce adverse effects attributed to the presence of the probes 630 within the vessels 614.

It will be understood that various aspects or details of the invention may be changed without departing from the scope of the invention. Furthermore, the foregoing description is for the purpose of illustration only, and not for the purpose of limitation—the invention being defined by the claims.

What is claimed is:

1. A system for making optics-based measurements on liquid samples, the system comprising:
    a fiber-optic probe comprising:
        a first body portion;
        a second body portion oriented at a ninety-degree angle relative to the first body portion and comprising an optical signal-transmitting window, an optical signal-reflecting boundary spaced from the optical signal-transmitting window, and a plurality of apertures between the optical signal-transmitting window and the optical signal-reflecting boundary, wherein the optical signal-transmitting window and the optical signal-reflecting boundary define a liquid sampling region therebetween in fluid communication with the plurality of apertures;
        a first optical fiber extending through the first body portion and the second body portion and terminating at a first fiber end in optical communication with the optical signal-transmitting window;
        a second optical fiber extending through the first body portion and the second body portion and terminating at a second fiber end in optical communication with the optical signal-transmitting window, wherein the optical signal-transmitting window seals the first optical fiber and the second optical fiber from the liquid sampling region; and
    a dissolution test apparatus comprising a vessel and a probe support component supporting the fiber-optic probe in a fixed orientation relative to the vessel,
    wherein at the fixed orientation, the first body portion is disposed along a vertical direction, the second body component is disposed along a horizontal direction, at least one of the apertures is disposed about a vertical axis offset from the first body portion by a horizontal distance, the at least one aperture establishes a flow path for bubbles and particulates out from the liquid sampling region generally along the vertical axis without obstruction by the fiber-optic probe, and the fiber-optic probe establishes an optical path through the first optical fiber, through the optical signal-transmitting window along the horizontal direction, through the liquid sampling region while intersecting the flow path, to the optical signal-reflecting boundary, reflecting from the optical signal-reflecting boundary back through the liquid sampling region, back through the optical signal-transmitting window along the horizontal direction, and through the second optical fiber.

2. The system of claim 1, wherein the second body portion is submerged in a liquid contained in the vessel.

3. The probe of claim 2, wherein the liquid includes a sample analyte at a concentration correlating to the attenuation of an optical signal passing through the liquid sampling region along the optical path.

4. The system of claim 1, wherein the vessel is one of a plurality of vessels, the fiber-optic probe is one of a plurality of fiber-optic probes respectively comprising a first optical fiber and a second optical fiber, and the probe support component supports the fiber-optic probes in a fixed orientation relative to the respective vessel.

5. The system of claim 1, wherein the probe support component is selected from the group consisting of (a) a vessel cover fitted to a vessel opening of the vessel and (b) a movable assembly configured for alternately inserting the fiber-optic probe into the vessel and removing the fiber-optic probe from the vessel.

6. The system of claim 1, further comprising a light source optically communicating with the first optical fiber, and a detector optically communicating with the second optical fiber and configured for converting optical signals into electrical signals indicative of analyte concentration in the liquid sampling region.

7. The system of claim 6, wherein the probe is one of a plurality of probes respectively comprising a first optical fiber and a second optical fiber, each first optical fiber communicates with the light source, and each second optical fiber communicates with the detector.

8. The system of claim 7, wherein the detector includes a plurality of detector units and each second fiber communicates with a respective detector unit.

9. A method for making optics-based measurements on liquid samples, the method comprising:
    dissolving analytes and dispersing particulates into a dissolution medium contained in a vessel by introducing an analyte-inclusive sample into the dissolution medium;
    inserting a fiber-optic probe into the dissolution medium such that a liquid sample region of the fiber-optic probe is submerged in the dissolution medium, and at a fixed orientation in which a first body portion of the fiber-optic probe is disposed along a vertical direction, a second body portion of the fiber-optic probe comprising the liquid sampling region is disposed along a horizontal direction, and an aperture communicating with the liquid sampling region is disposed about a vertical axis offset from the first body portion by a horizontal distance, wherein bubbles and particulates are purged from the liquid sample region along a generally vertical flow path through the aperture without being obstructed by the fiber-optic probe;

transmitting an optical signal of a first intensity through a first optical fiber running through the first probe body along a first optical transmitting path, through the second probe body along a horizontal second optical transmitting path angled relative to the first optical transmitting path, and to the liquid sampling region;

transmitting the optical signal through the liquid sampling region predominantly along the horizontal direction, reflecting the optical signal off of a optical signal-reflecting boundary of the second probe body, and transmitting the optical signal back through the liquid sampling region predominantly along the horizontal direction to produce an optical signal of a second intensity, the second intensity being attenuated relative to the first intensity in proportion to a concentration of analytes in the liquid sample region;

transmitting the optical signal of the second intensity from the liquid sampling region and through a second optical fiber running through the second probe body along a horizontal first optical receiving path and through the second probe body along a second optical receiving path angled relative to the first optical receiving path, and to an optical detector; and acquiring analyte concentration data by correlating the optical signal received at the detector with a concentration of analytes in the liquid sample region.

10. The method of claim 9, wherein submerging inserting includes affixing the probe to a vessel cover fitted to a vessel opening of the vessel.

11. The method of claim 9, wherein submerging inserting includes operating a movable head assembly of a dissolution test apparatus to lower the probe into the vessel.

12. The method of claim 11 further including, after transmitting the optical signal of the second intensity through the second optical fiber, operating the movable assembly to raise the probe out from the vessel.

13. The method of claim 9, further including generating dissolution rate data based on the acquired analyte concentration data.

* * * * *